(12) United States Patent  (10) Patent No.: US 7,720,193 B2
Tani et al.  (45) Date of Patent:  May 18, 2010

(54) X-RAY FLUORESCENCE ANALYSIS TO DETERMINE LEVELS OF HAZARDOUS SUBSTANCES

(75) Inventors: Yoshiyuki Tani, Osaka (JP); Hiroshi Iwamoto, Osaka (JP); Takao Hisazumi, Osaka (JP); Yukihiro Iwata, Osaka (JP)

(73) Assignee: Panasonic Corporation, Osaka (JP)

( * ) Notice: Subject to any disclaimer, the term of this patent is extended or adjusted under 35 U.S.C. 154(b) by 149 days.

(21) Appl. No.: 12/064,624

(22) PCT Filed: Aug. 14, 2006

(86) PCT No.: PCT/JP2006/316283

§ 371 (c)(1),
(2), (4) Date: Feb. 22, 2008

(87) PCT Pub. No.: WO2007/023751

PCT Pub. Date: Mar. 1, 2007

(65) Prior Publication Data

US 2009/0262890 A1  Oct. 22, 2009

(30) Foreign Application Priority Data

Aug. 23, 2005 (JP) ............................. 2005-241153

(51) Int. Cl.
*G01N 23/223* (2006.01)
(52) U.S. Cl. .......................................... 378/48; 378/45
(58) Field of Classification Search ................... 378/48, 378/45
See application file for complete search history.

(56) References Cited

U.S. PATENT DOCUMENTS 4,104,526 A   8/1978   Albert (Continued)

FOREIGN PATENT DOCUMENTS

JP   7-049317   2/1995

(Continued)

OTHER PUBLICATIONS

Shirvastava et al. "Handheld X-ray Fluorescence: Practical Application as a Screening tool to Detect the Presence of Environmentally-Sensitive Substances in Electronic Equipment", Electronics and the Environment, 2005 Proceedings of the 2005 IEEE International Symposiums on New Orleans, pp. 157-162.

(Continued)

*Primary Examiner*—Edward J Glick
*Assistant Examiner*—Thomas R Artman
(74) *Attorney, Agent, or Firm*—McDermott Will & Emery LLP (57) ABSTRACT

An object of the present invention is to shorten the time required by processing, and to simplify the work and increase the number of samples processed, in the X-ray analysis of a specific substance contained in a sample. To achieve the object, a method for assaying the content of a specific substance in a sample 106, comprises a measurement step (S3) of irradiating the sample 106 with X-rays, and measuring the spectrum of the sample 106, and an assay step (S4) of comparing the components of the specific substance in the spectrum of the sample 106 and in a reference spectrum that has been pre-stored for the sample 106, and determining whether the specific substance is contained in the sample 106 in an amount equal to or greater than a specific value.

9 Claims, 4 Drawing Sheets

U.S. PATENT DOCUMENTS

| | | | |
|---|---|---|---|
| 5,663,997 A * | 9/1997 | Willis et al. | 378/45 |
| 6,519,315 B2 * | 2/2003 | Sommer et al. | 378/45 |
| 6,765,205 B2 * | 7/2004 | Ochiai et al. | 850/9 |
| 7,170,970 B2 * | 1/2007 | Tani et al. | 378/45 |
| 7,449,682 B2 * | 11/2008 | Larson et al. | 250/281 |

FOREIGN PATENT DOCUMENTS

| | | |
|---|---|---|
| JP | 7-063707 | 3/1995 |
| JP | 2005-003440 | 1/2005 |
| JP | 2006-10603 | 1/2006 |
| JP | 2006-38757 | 2/2006 |

OTHER PUBLICATIONS

IEC ACEA ad hoc working Group, "Procedures for the Determination of Levels of regulated Substances in Electrotechnical Products", XP 002402826, pp. 1-79, Jun. 12, 2004.

* cited by examiner

X-RAY FLUORESCENCE ANALYSIS TO DETERMINE LEVELS OF HAZARDOUS SUBSTANCES

This application is the U.S. National Phase under 35 U.S.C. §371 of International Application No. PCT/JP2006/316283, filed on Aug. 14, 2006, which in turn claims the benefit of Japanese Application No. 2005-241153, filed on Aug. 23, 2005, the disclosures of which Applications are incorporated by reference herein.

TECHNICAL FIELD

The present invention relates to a method and apparatus for assaying the content of a specific substance used in fluorescent X-ray analysis.

BACKGROUND ART

In the field of industry, heavy metal- and bromine-based flame retardants and so forth in various materials and products have been indicated to be hazardous to humans and the environment, and the regulation of harmful substances has been growing around the world. For instance, in Europe, the "Directive on the restriction of the use of certain hazardous substances in electrical and electronic equipment (RoHS Directive)" prohibits the use of parts containing more than 100 ppm cadmium (Cd) or more than 1000 ppm lead (Pb), mercury (Hg), certain bromine-based flame retardants (polybrominated biphenyls (PBB) or polybrominated biphenyl ethers (PBDE)), or hexavalent chromium (Cr (VI)). Accordingly, it is absolutely essential that manufacturers of electrical and electronic equipment confirm that the various parts they make do not contain more than the regulated amounts of hazardous substances.

In general, the content of a hazardous substance such as an environmental hazardous substance is assayed or measured by performing quantitative analysis. In this quantitative analysis, fluorescent X-ray analysis is utilized because it makes compositional analysis possible on the order of a few tens of parts per million, and allows non-destructive measurement. Quantitative analysis featuring fluorescent X-ray analysis is used to assay contents in many other fields as well (see Patent Documents 1 and 2, for example).

With the above-mentioned conventional assay methods, quantitative analysis is performed on all parts that are supposed to be assayed, regardless of whether or not any environmental hazardous substances or other hazardous substances are actually contained, so detailed analysis ends up being performed even on parts containing no hazardous substances, which wastes time in the processing step. For example, it takes about 12 minutes to perform quantitative analysis of five elements for a single part. Consequently, it is desirable to eliminate unnecessary processing and shorten the processing time, particularly in processing steps involving a large quantity of parts. Also, since the analysis results are outputted as numerical values, the operator has to visually confirm the values and make a decision about the content, which imposes a significant burden on the operator.

Furthermore, if the sample is a composite part composed of a plurality of materials, determining by X-ray analysis which of the parts in the composite part contains the hazardous substance requires that the composite part be taken apart to its constituent parts composed of single materials prior to analysis. Therefore, the time it takes for disassembly and the burden on the operator are major obstacles.

Patent Document 1: Japanese published unexamined patent Application No. H7-49317
Patent Document 2: Japanese published unexamined patent Application No. H7-63707

DISCLOSURE OF THE INVENTION

It is an object of the present invention to provide a method and apparatus for assaying a specific substance, such as a hazardous substance, and thereby solve the above-mentioned problems.

The method for assaying the content of a specific substance in a sample comprises a measurement step and an assay step. In the measurement step, the sample is irradiated with X-rays, and a spectrum of the sample is measured. In the assay step, the components of the specific substance are compared in the spectrum of the sample and in a reference spectrum that has been pre-stored for that sample, and whether the specific substance is contained in the sample in an amount equal to or greater than a specific value is determined.

The "sample" here is, for example, an electrical or electronic portion for which it is necessary to determine a specific substance is contained. The "specific substance" is, for example, an environmental hazardous substance (more specifically, an element group specified in the RoHS Directive). The "reference spectrum that has been pre-stored" is, for example, the spectrum of a sample that has been measured in the past and deemed not to contain the specific substance. This spectrum is put into a database upon every measurement, for each sample. The "specific value" may, for example, be within the upper limit of the permissible range of content for the specific substance, and is preferably set for each part, or each measurement, prior to the assay step. This method can also be applied, for example, to the assay of the content of a specific substance using fluorescent X-ray analysis. Therefore, in that case, "spectrum" will refer to the fluorescent X-ray spectrum.

With a conventional method, a problem was that quantitative analysis had to be performed on a sample regardless of whether or not it contained the specific substance, so processing took more time.

With this method, however, it is possible to determine whether or not the sample is contained in an amount equal to or greater than a specific value by comparing the spectrum of the sample with a reference spectrum. Therefore, how long processing takes can be shortened by comparing assays made using quantitative analysis. Furthermore, this facilitates the work entailed by the step, and increases the number of samples that can be processed.

The method for assaying the content of a specific substance, wherein the sample is a composite part composed of a plurality of materials.

Here, "a plurality of materials" includes, for example, metals and plastics, and when the parts of the sample have been plated. "Composite part" here may be, for example, one in which a plurality of parts composed of different materials are combined and constitute separate parts, or may be a completed part.

With a conventional method, in assaying the content of a specific substance in a composite part, first, the composite part had to be taken apart into single parts composed of single materials, after which the assay was performed. Consequently, the overall process took a long time and imposed a heavy burden on the operator.

With this method, meanwhile, whether or not a composite part contains a specific substance can be determined without having to take it apart. Specifically, since parts can be classified into those that contain a specific substance and those that do not, the number of composite parts that have to be taken apart can be reduced. Therefore, the processing of specific substances in which the handling of a large quantity of composite parts is required can be streamlined.

The method for assaying the content of a specific substance, wherein the sample is an environmental hazardous substance.

The "environmental hazardous substance" here is, for example, an element group indicated by the RoHS Directive, the content of which needs to be assayed.

The method for assaying the content of a specific substance, wherein the environmental hazardous substance contains one or more of cadmium, lead, mercury, bromine, and chromium.

It is particularly likely that these five elements will be contained in the sample pertaining to the present invention, and determining whether they are contained is particularly necessary.

The method for assaying the content of a specific substance, wherein the assay step further includes a confirmation step of comparing the main components in the spectrum of the sample and in the reference spectrum, and confirming that the reference spectrum is one that corresponds to the sample.

"Main components" here may be, for example, any pronounced peaks of components other than the specific substance (such as metals or plastics that are primary constituent components), which appear in the sample spectrum and the reference spectrum.

Including this step in the assay method of the present invention lowers the incidence of mistakenly using the wrong sample spectrum as the reference spectrum, and allows the assay to be performed with greater certainty.

The method for assaying the content of a specific substance, wherein the reference spectrum is a reference spectrum correlated to an identification number of the sample.

The "identification number" here may be, for example, a part number.

Identification numbers made up of numerals and so forth are usually allotted to part groups of electrical and electronic products. Therefore, this identification number is stored ahead of time along with the corresponding reference spectrum, and a reference spectrum having the same identification number as that of the sample is called up.

With this method, a reference spectrum corresponding to the sample can be called up with greater certainty, which makes the processing more efficient.

The method for assaying the content of a specific substance, wherein the measurement step includes obtaining the reference spectrum measurement conditions, and using the obtained measurement conditions to measure the spectrum of the sample.

The "measurement conditions" here are, for example, the X-ray irradiation time or X-ray intensity.

With this method, the measurement conditions in the irradiation of the sample with X-rays are combined with the measurement conditions for the reference spectrum, which makes it possible to compare the sample spectrum and the reference spectrum properly and makes the processing more efficient.

The method for assaying the content of a specific substance, wherein the reference spectrum measurement conditions are measurement conditions for a reference spectrum correlated to an identification number of the sample.

With this method, attention is focused on the fact that the above-mentioned identification number is utilized in calling up the reference spectrum, and the identification number is also utilized in calling up the measurement conditions. The processing is therefore more efficient.

The method for assaying the content of a specific substance, wherein more detailed measurement is performed on a sample that has been determined to contain at least a certain amount of the specific substance.

The phrase "more detailed measurement" here may, for example, be X-ray quantitative analysis in which the content of the sample is quantitatively measured. At this stage, if the sample is a composite part composed of a plurality of materials, it is preferably taken apart down to single parts composed of single materials.

Based on the results obtained with this method, it is possible to ascertain the quantitative amount of a specific substance by performing more detailed analysis (such as the above-mentioned conventional quantitative analysis) on a sample that has been selected from a large number of samples by being deemed to contain the specific substance in an amount equal to or greater than a specific value.

The assay apparatus for assaying the content of a specific substance in a sample comprises an X-ray tube, a detector, a memory unit, and a computing controller. The X-ray tube is for irradiating the sample with X-rays, and the detector is for detecting X-rays emitted from the sample. The memory unit is for storing a reference spectrum corresponding to the sample. The computing controller is for finding the spectrum of the sample on the basis of the X-rays detected by the detector, comparing the components of the specific substance in the sample spectrum and in a reference spectrum stored in the memory component, and determining whether or not the specific substance is contained in the sample in an amount equal to or greater than a specific value.

The "sample" here is, for example, an electrical or electronic portion that needs to be assayed for its content of a specific substance. The "specific substance" is, for example, an environmental hazardous substance (more specifically, an element group specified in the RoHS Directive). The "reference spectrum that has been pre-stored" is, for example, the spectrum of a sample that has been measured in the past and deemed not to contain the specific substance. This spectrum is put into a database upon every measurement, for each sample, in a form correlated to an identification number that allows the sample to be specified. The "specific value" may, for example, be within the upper limit of the permissible range of content for the specific substance, and is preferably set for each part, or each measurement, prior to the assay step. This apparatus can also be applied, for example, to the assay of the content of a specific substance using fluorescent X-ray analysis. Therefore, in that case, "spectrum" will refer to the fluorescent X-ray spectrum.

With a conventional apparatus, a problem was that quantitative analysis had to be performed on a sample regardless of whether or not it contained the specific substance, so processing took more time.

With this apparatus, however, it is possible to determine whether or not the sample is contained in an amount equal to or greater than a specific value by comparing the spectrum of the sample with a reference spectrum. Therefore, how long processing takes can be shortened by comparing assays made using quantitative analysis. Furthermore, this facilitates the work entailed by the step, and increases the number of samples that can be processed.

With the present invention, as compared to a conventional assay method, the time it takes to perform an assay step of determining whether the specific substance is contained in the sample in an amount equal to or greater than a specific value can be shortened, the work entailed by the step can be simplified, and more samples can be processed.

NUMERICAL REFERENCES 100 content assay apparatus
101 input unit
102 computing controller
103 controller
104 X-ray tube
105 primary rays
106 sample
107 fluorescent X-rays
108 detector
109 amplifier
110 display unit
111 memory unit

DETAILED DESCRIPTION OF THE PREFERRED EMBODIMENT

Embodiments of the present invention will now be described through reference to the drawings. In the following embodiments, the sample will be assumed to be a single part composed of a single material.

<Structure of Content Assay Apparatus>

The structure of the content assay apparatus will now be described through reference to FIG. 1.

Figure 1:
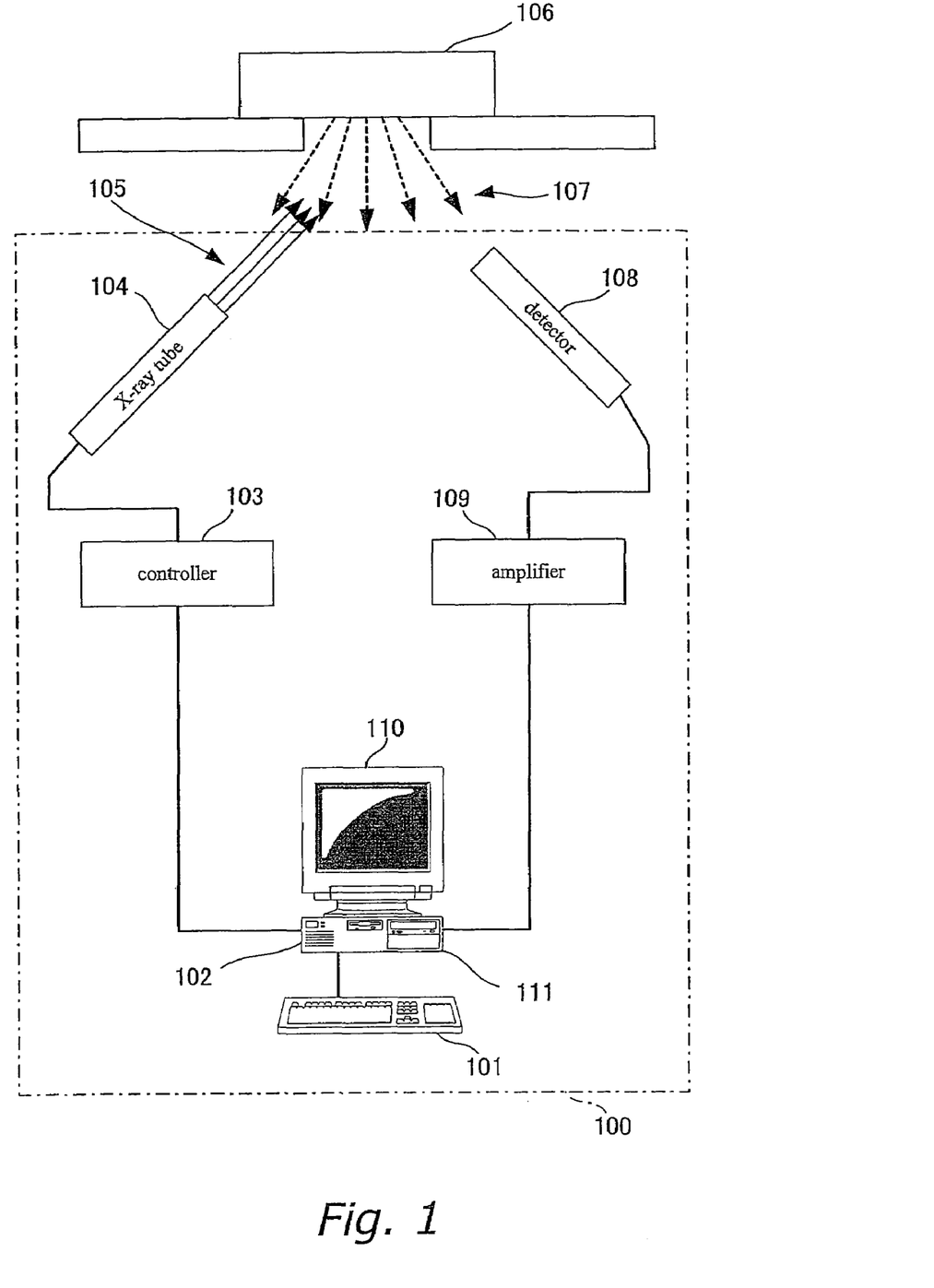
FIG. 1 is a simplified diagram of an example of the content assay apparatus of the present invention.

FIG. 1 is a simplified diagram of the apparatus 100 for assaying the content of a specific substance.

The content assay apparatus 100 is a fluorescent X-ray analysis apparatus comprising of an input unit 101, a computing controller 102, a controller 103, an X-ray tube 104, a detector 108, an amplifier 109, a display unit 110, and a memory unit 111.

The input unit 101 comprises of a keyboard or the like for inputting information related to a sample 106. The sample 106 here is an electrical or electronic portion, for example. The "information related to the sample 106" is, for example, the part number of the sample 106, or the measurement conditions for the sample 106. The computing controller 102 subjects the measurement conditions to signal processing, and executes computation for finding the spectrum of the sample 106. The controller 103 controls the voltage and current applied to the X-ray tube, and on the basis of this, the X-ray tube 104 emits X-rays which irradiate the sample as primary rays 105. As a result, fluorescent X-rays 107 are emitted from the sample 106, the detector 108 detects the luminous energy of the fluorescent X-rays 107, which gives a detection signal. The amplifier 109 amplifies this detection signal. The computing controller 102 finds the spectrum from the amplified detection signal, compares this spectrum with a reference spectrum, and assays the content of a specific substance (this will be described in detail below). The display unit 110 outputs and displays the assay result and so forth.

The memory unit 111 stores information about the sample 106, computation results, a reference spectrum database, and so on. The reference spectrum database comprises of spectra for each part that has been measured in the past and deemed not to contain a specific substance. The memory unit 111 may also store all of the measured numerical data as spectrum data, and may store the peak positions of main units, peak heights, and other important data.

<Assay Operation>

The operation of the assay will now be described through reference to FIGS. 2, 3A, 3B and 3C.

Figure 2:
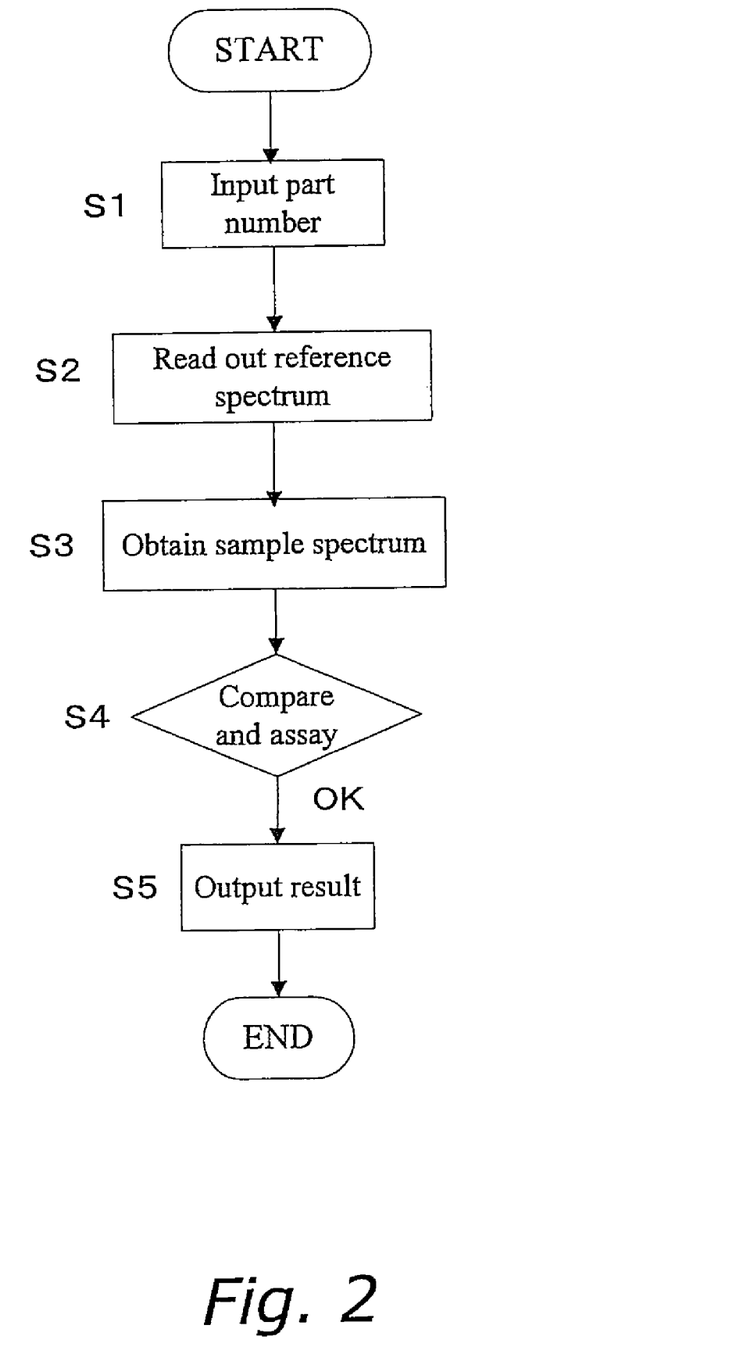
FIG. 2 is a flowchart of the assay method pertaining to an embodiment of the present invention.
Figure 3A:
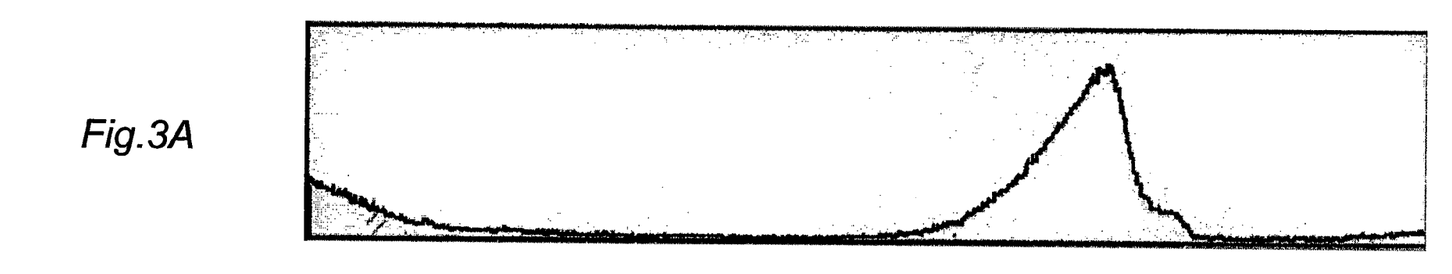
FIGS. 3A, 3B and 3C are examples of the spectral data pertaining to an embodiment of the present invention.
Figure 3B:
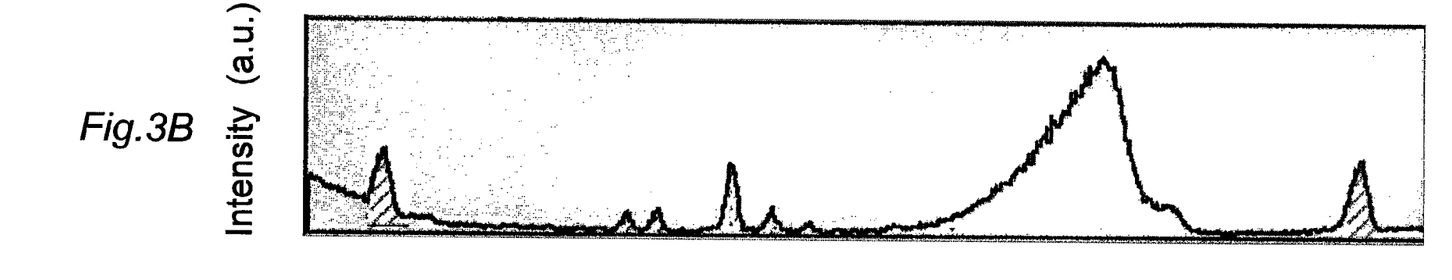
Figure 3C:
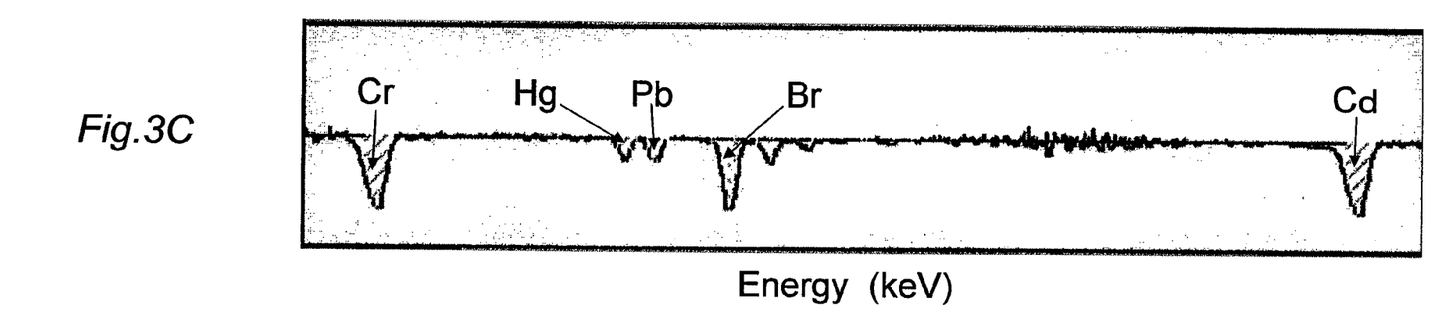

FIG. 2 is a flowchart of the assay method pertaining to this embodiment. FIGS. 3A, 3B and 3C are examples of the spectral data used in this embodiment. FIG. 3A is an example of the reference spectrum, FIG. 3B is an example of the spectrum of the sample 106 (hereinafter referred to as sample spectrum), and FIG. 3C is an example of the differential spectrum between the above two spectra. The specific substance here is assumed to be an environmental hazardous substance.

First, when the part number of the sample 106 is inputted from the input unit 101 (S1), a reference spectrum such as that shown in FIG. 3A, corresponding to the part number, is read out from the reference spectrum database stored in the memory unit 111 (S2).

Meanwhile, the sample 106 is irradiated with X-rays and the spectrum of the sample 106, which is shown in FIG. 3B, is obtained by the computing controller 102 (S3). The computing controller 102 then compares the difference between the reference spectrum and the sample spectrum, and determines whether or not an environmental hazardous substance is contained, using as a reference whether it is contained in an amount equal to or greater than a specific value (S4). The difference may be examined by finding the difference between the two spectra as shown in FIG. 3C. The compared parameters include the peak position of the environmental hazardous substance, the peak height, and so forth. This allows a determination as to the content of an environmental hazardous substance to be made easily. Finally, this result is outputted to the display unit 110 (S5). Either step S2 or S3 may be performed first.

Whether or not an environmental hazardous substance is contained can be ascertained by the above method. Based on this result, only enough samples to determine the amount contained can be selected from among a large number of samples. This is what is known as screening. Also, by outputting the result of whether the substance is contained or not, the operator can check the result at a glance, so the presence of this substance can be ascertained more easily than by a conventional confirmation method based on a numerical value.

Therefore, with this embodiment, measuring a single part takes less time and less work than with a conventional assay method, allowing more samples to be processed.

Other Embodiments

An embodiment of the present invention was described above, but the present invention is not limited to the above embodiment, and various modifications are possible without deviating from the gist of the present invention.

(A)

In the above embodiment, an electrical or electronic portion selected by being deemed to contain an environmental hazardous substance may be subjected to even more detailed measurement.

The "more detailed measurement" here may be, for example, X-ray quantitative analysis in which the content of the sample is quantitatively measured, and may be performed after the output of the result (S5). This allows the content to be determined and allows a quantitative evaluation of the specific substance contained in the sample.

(B)

In the above embodiment, the electrical or electronic portion used as the sample was composed of a single material, but may instead be a composite part composed of a plurality of materials (such as metals and plastics, and when the parts of the sample have been plated). Specifically, a plurality of parts composed of different materials may be combined and constitute separate parts, or this may be a completed part, such as a plastic unit that has been plated. In general, in assaying the content of a composite part, the part must first be taken apart down to single parts composed of single materials. Therefore, with a conventional method, since measurement is performed after all of the samples have been taken apart, the total processing takes a long time and this imposes a heavy burden on the operator.

With the present method, even with a composite part, it is possible to check whether or not a specific substance is contained without ever having to take apart the composite part, which means that fewer composite parts have to be taken apart. As a result, the processing of specific substances in which a large number of parts are handled can be streamlined.

Here, the reference spectrum used in the assay step of this modification may, for example, be a spectrum obtained by X-ray analysis of a part that is the same as a single part constituting a sample, or a part that is combined with a single part which does not contain the specific substance and that is the same as the composite part that is the sample, or a completed part.

When the above-mentioned step A is performed on an electrical or electronic portion selected by being deemed to contain an environmental hazardous substance, then the sample is preferably taken apart down to single parts composed of single materials prior to step A.

(C)

Figure 4:
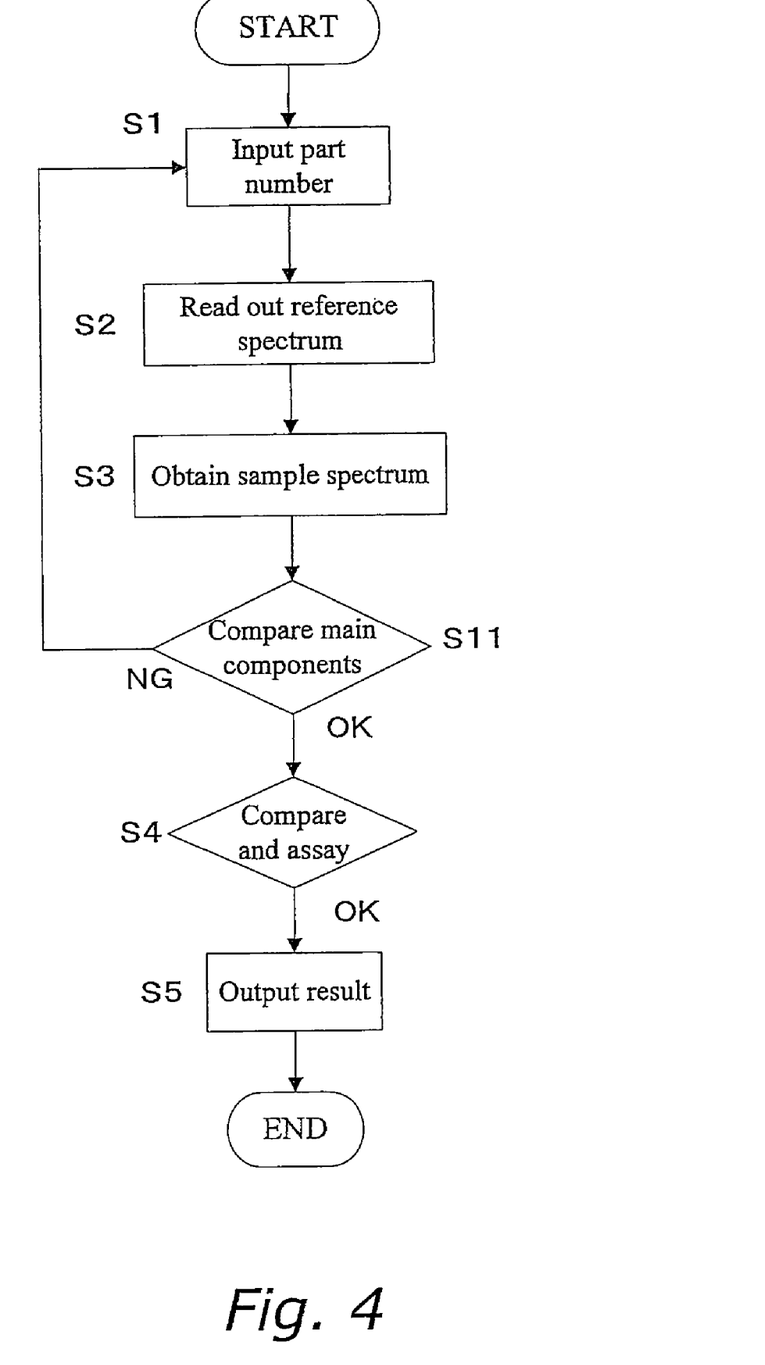
FIG. 4 is a flowchart of the assay method pertaining to another embodiment of the present invention.

FIG. 4 is a flowchart of the assay method pertaining to a modification of the present invention.

In the above embodiment, in step S2, the reference spectrum corresponding to a part number was read out from a reference spectrum database stored in the memory unit 111. However, it is conceivable that the reference spectrum could be read out for a different part than the electrical or electronic portion to be assayed, due to a mistake in inputting the part number, for example. In view of this, a step may be performed of confirming that the reference spectrum that has been read out is the desired spectrum (S11).

In S11, the main components are compared in the sample spectrum and the reference spectrum, and it is confirmed that the correct reference spectrum has been read out. The "main components" here may be, for example, any pronounced peaks, such as those of a distinctive metal of the electrical or electronic portion, other than the environmental hazardous substance that is the specific substance, which appear in the two spectra.

Including this step in the assay method of the present invention lowers the incidence of mistakenly using the spectrum of a part other than the intended sample as a reference, and allows the specific substance content to be assayed with greater certainty.

(D)

The measurement conditions for the reference spectrum stored in the memory unit 111 may be used as the measurement conditions in step S3 for obtaining a sample spectrum in the above-mentioned embodiment. Here, if the X-ray irradiation time, X-ray intensity, and other initial conditions are made the same, the sample spectrum and the reference spectrum can be properly compared, and processing will be more efficient.

(E)

In the above embodiment, five main elements were listed as environmental hazardous substances serving as the specific substance to be assayed for being contained, but the assay is not limited to these. For example, the effect of the present invention will be obtained with other hazardous substances, such as gold, silver, platinum, and palladium, by the same method.

(F)

In the above embodiment, the example given was of the memory unit 111 being built into the content assay apparatus 100, but the structure is not limited to this. For example, the memory unit 111 may be an external storage device connected by cable or the like to the content assay apparatus 100.

(G)

In the above embodiment, the example given was of the reference spectrum database being stored in the memory unit 111, but the configuration is not limited to this. For example, the database may be stored in an external storage medium, and the external storage medium connected by cable or the like to the content assay apparatus 100.

(H)

In the above embodiment, the example given was of the result output being displayed on the display unit 110, but the configuration is not limited to this. For example, the result may be outputted on paper.

INDUSTRIAL APPLICABILITY

The specific substance content assay method and apparatus pertaining to the present invention can be applied in a wide range of fields in which the amount of elements contained is measured, and in which it is necessary to shorten the time required by processing, and to simplify the work and increase the number of samples processed.

The invention claimed is:

1. A method for assaying the content of a specific substance in a sample, comprising:
    a measurement step of irradiating the sample with X-rays, and measuring a spectrum of the sample; and
    an assay step of comparing the components of the specific substance in the spectrum of the sample and in a reference spectrum that has been pre-stored for that sample, and determining whether the specific substance is contained in the sample in an amount equal to or greater than a specific value,
    wherein the reference spectrum is a reference spectrum correlated to an identification number of the sample.

2. The method for assaying the content of a specific substance according to claim 1, wherein the sample is a composite part composed of a plurality of materials.

3. The method for assaying the content of a specific substance according to claim 1, wherein the sample is an environmental hazardous substance.

4. The method for assaying the content of a specific substance according to claim 3, wherein the environmental hazardous substance includes at least one of cadmium, lead, mercury, bromine, and chromium.

5. The method for assaying the content of a specific substance according to claim 1, wherein the assay step further includes a confirmation step of comparing the main components in the spectrum of the sample and in the reference spectrum, and confirming that the reference spectrum is one that corresponds to the sample.

6. The method for assaying the content of a specific substance according to claim 1, wherein the measurement step includes obtaining the reference spectrum measurement conditions, and using the obtained measurement conditions to measure the spectrum of the sample.

7. The method for assaying the content of a specific substance according to claim 6, wherein the reference spectrum measurement conditions are measurement conditions for the reference spectrum correlated to the identification number of the sample.

8. The method for assaying the content of a specific substance according to claim 1, wherein more detailed measurement is performed on a sample that has been determined to contain at least a certain amount of the specific substance.

9. An assay apparatus for assaying the content of a specific substance in a sample, comprising:
    an X-ray tube for irradiating the sample with X-rays;
    a detector for detecting X-rays emitted from the sample;
    a memory unit for storing a reference spectrum corresponding to the sample; and
    a computing controller for finding the spectrum of the sample on the basis of the X-rays detected by the detector, comparing the components of the specific substance in the sample spectrum and in a reference spectrum stored in the memory unit, and determining whether or not the specific substance is contained in the sample in an amount equal to or greater than a specific value,
    wherein the reference spectrum is a reference spectrum correlated to an identification number of the sample.

* * * * *